United States Patent [19]

Fraser

[11] 4,197,658
[45] Apr. 15, 1980

[54] TISSUE FREEZE DRYER

[75] Inventor: Douglas S. Fraser, New Paltz, N.Y.

[73] Assignee: FTS Systems, Inc., Stone Ridge, N.Y.

[21] Appl. No.: 905,426

[22] Filed: May 12, 1978

[51] Int. Cl.² ............................................. F26B 13/30
[52] U.S. Cl. ......................................................... 34/92
[58] Field of Search ........................................ 34/5, 92

[56] References Cited

U.S. PATENT DOCUMENTS

| | | | |
|---|---|---|---|
| 3,451,189 | 6/1969 | Taggart | 34/92 |
| 3,639,999 | 2/1972 | Adams | 34/92 |
| 4,020,563 | 5/1977 | Hoefer | 34/92 |

*Primary Examiner*—John J. Camby

*Attorney, Agent, or Firm*—Robert E. Wagner; Gerald T. Shekleton

[57] ABSTRACT

A freeze dryer for rapidly and efficiently drying tissue specimens, having a source of heat independent of the cover and mounted for efficient heat transfer to a copper support plate having a substantially flat top surface. A specimen plate is machined from aluminum to have a recessed bottom surface which is matable with the support plate for maximum physical contact. The specimen plate has peripheral walls of a thickness and a height that will eliminate substantially all heat differentials between different portions of the specimen plate interior caused by external variations to allow effective control of the temperature of the specimen plate.

9 Claims, 3 Drawing Figures

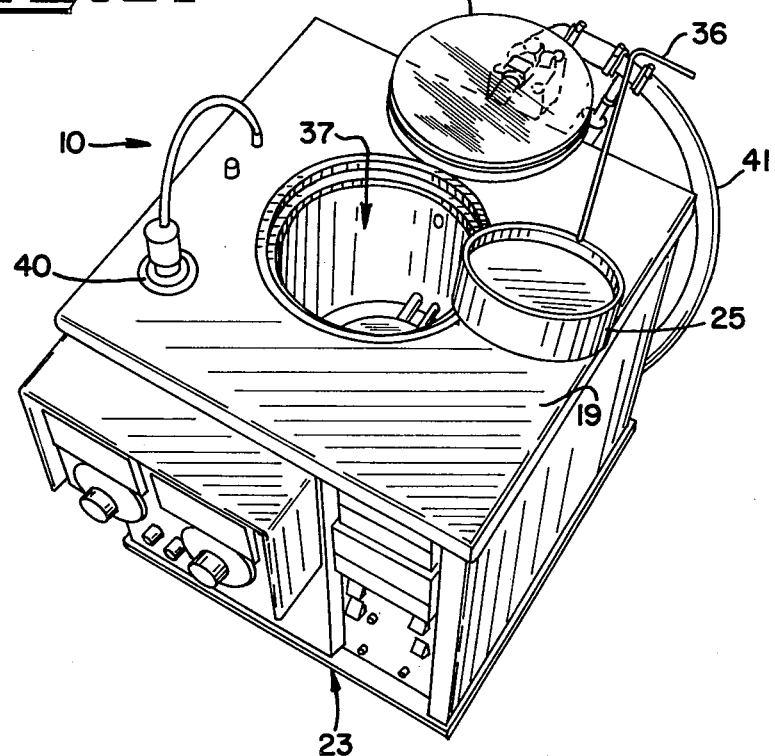
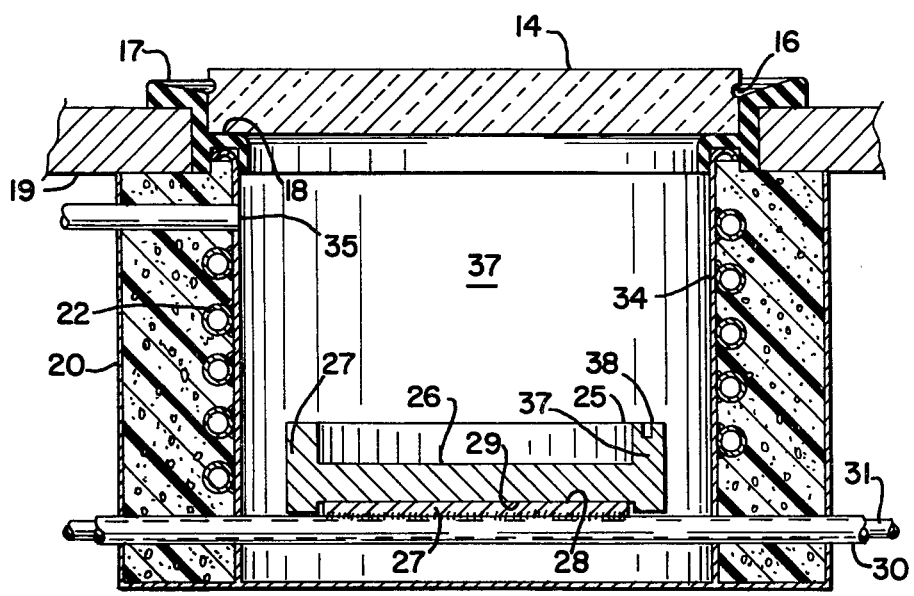

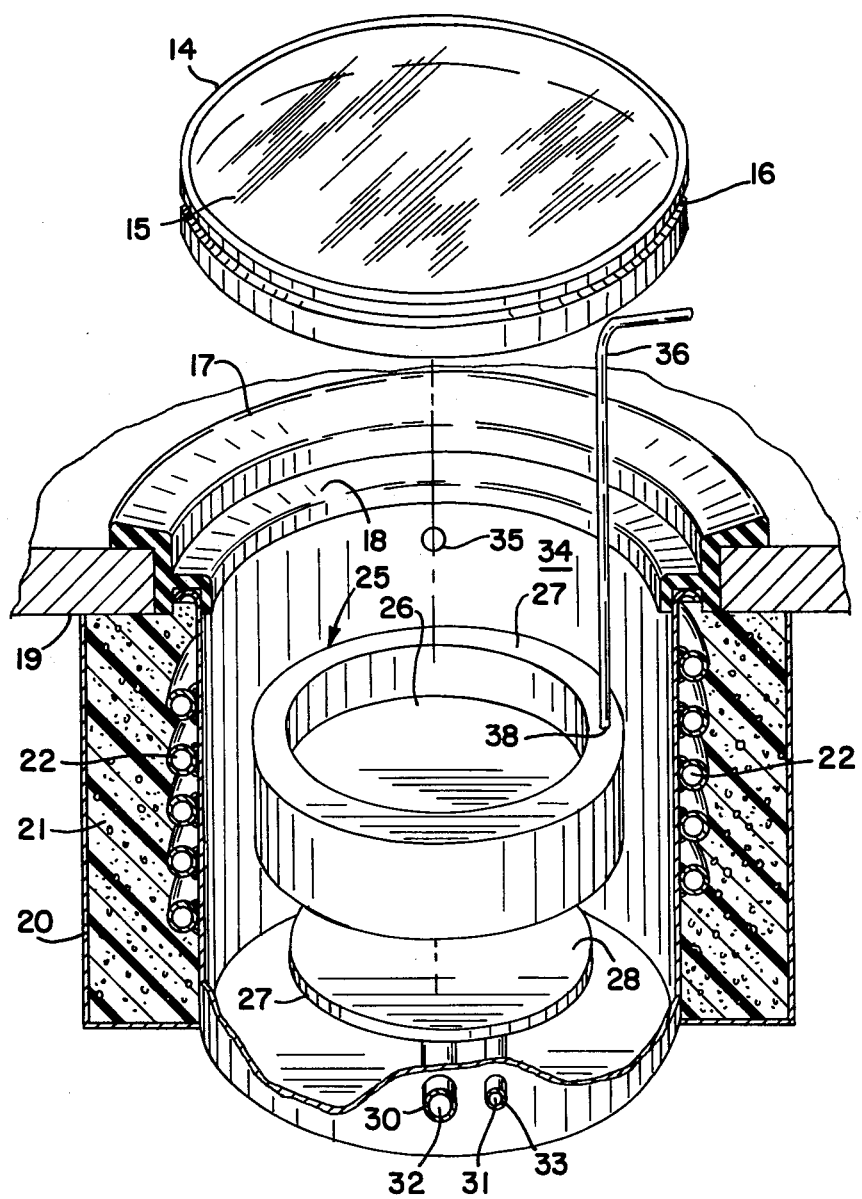
FIG_2

TISSUE FREEZE DRYER

BACKGROUND OF THE INVENTION

This application relates to a freeze dryer for histological use, and in particular, to a tissue freeze dryer for the preparation of paraffin or resin embedded tissues in a form suitable for easy storage and handling.

The preparation of tissue specimens in a form suitable for storage and study has traditionally been performed in a multitude of separate and discrete steps, each step requiring extensive handling with the attendant increased chances of contamination and other problems. In general, preparation of a tissue specimen involves the rapid removal of the tissue from the animal, freezing the tissue specimen at temperatures from −60° C. to −130° C. The frozen specimen is then dried by placement in a vacuum where the vacuum sublimates the water from the sample; liquid degassed paraffin or resin is then allowed to completely engulf and permeate the tissue specimen. The resin or paraffin cools and solidifies, after which the embedded tissue is removed and sectioned by a microtome or other means for study.

Should formaldahyde-induced-fluorescence (FIF) be desired, paraformaldahyde gas is allowed to permeate the vacuum chamber to allow absorption of the gas by the resin or paraffin.

To eliminate the problems of contamination or the like associated with performing these various procedures in separate operations, the apparatus of the type disclosed in U.S. Pat. No. 3,639,999 and that disclosed in Ser. No. 746,294, filed Dec. 1, 1976, now abandoned were developed. These assemblies allow the preparation of a resin embedded specimen to be accomplished within one assembly without the necessity of transference to another container or any other unnecessary handling once the tissue specimen has been cut from the animal. In assemblies of the type disclosed in the above art, the tissue sample is placed in a cup within the assembly; the degassed resin or paraffin is floated about the sample and solidified. The embedded specimen may then be removed from the assembly and sliced with a microtome for study, or it may be stored for future study in this condition.

In these tissue embedding assemblies of the prior art, a tissue support plate receives and supports a cup holder which has openings integrally formed for the reception of tissue holding cups. The holder is removable from the support plate to allow the easy removal and/or placement of the tissue holding cups in the opening. The support plate itself is heated through an internal resistance heater, connected to a source of power by wires passing through the cover. When embedding with paraffin, chunks of paraffin are dispersed on the support plate and, when melted, seep into perforated tissue holding cups to embed the tissue specimens. Hot spots and poor temperature control in the support plate are unavoidable when such a support plate is heated internally, as taught in the above-identified patents. These hot spots can cause foaming and decomposition of the paraffin, which in turn leads to deposits of paraffin decomposition products which can form on the support plate. These deposits decrease the heating efficiency, create further hot spots and can contaminate the embedded tissue specimens. With such apparatus of the prior art, the support plate was not easily removed for cleaning while its location within the freeze drying chamber did not permit effective cleaning within the chamber.

SUMMARY OF THE INVENTION

Therefore, an object of the subject invention is a new and improved resin and paraffin embedding assembly.

Another object of the subject invention is a resin and paraffin embedding assembly having a support plate which uniformly distributes heat to substantially all portions of the support plate.

A further object of the subject invention is a resin and paraffin embedding assembly which has a support plate which may be easily removed from the assembly for easy cleaning and placement of the tissue embedding cups.

Still another object of the subject invention is a paraffin and resin embedding assembly in which the temperature of the support plate may be accurately controlled.

These and other objects are attained in accordance with the present invention wherein there is provided an improved resin and paraffin embedding assembly. The assembly of the subject invention includes a copper support plate machined to precise tolerances to present a substantially flat upper surface and heated with an electrical resistance cartridge heater which may be removably mounted underneath and adjacent the support plate. A temperature sensor is similarly mounted. A tissue platen or specimen plate for containing the specimen containers is formed of aluminum and machined to mate with the tissue platen support plate.

The platen is of a thickness and has sufficiently high peripheral walls that will be capable of absorbing variations in ambient temperature and therefore will contribute to the control of the temperature of any object on its surface, in addition to substantially eliminating hot spots and other lesser variations of temperature on the surface of the tissue platen.

The lower surface of the tissue platen is recessed to provide a downwardly extending lip which serves to both locate the tissue platen on the support plate and to assure more efficient transfer of heat from the support plate to the tissue platen. Maximum contact between the tissue platen and the support plate is attained through the use of a silicone grease which is wiped onto the support plate to form a thin substantially uniform layer. Placement of the tissue platen onto the support plate is made with a slight twisting motion that insures maximum contact between the opposing surfaces for maximum and uniform thermal transfer.

Refrigerant coils surround the freeze drying chamber and condense any vapors emanating from the tissue and the resin or paraffin. The top circumference of the chamber is lined with a rim gasket of a resilient material on which a solid, clear acrylic top plate rests. Under vacuum, the clear top plate is biased against the rim gasket and affords a vacuum tight seal. An opening is provided in an upper wall portion of the freeze drying chamber and through this opening the chamber interior is in communication with a vacuum pump, preferably through a three-way valve such as that disclosed in U.S. Pat. No. 3,945,607 which provides an alternate opening and closing of the connection to the vacuum pump and the ambient air. While the subject invention will be described in relation to a paraffin embedding assembly, it should be realized that resin embedding assemblies may also utilize the subject invention, upon the substitution of the appropriate cover assembly, such as that described in the application of U.S. Ser. No. 746,294, filed Dec. 1, 1976, now abandoned.

DESCRIPTION OF THE DRAWINGS

Further objects of the invention, together with additional features contributing thereto and advantages accruing therefrom, will be apparent from the following description of one embodiment of the invention when read in conjunction with the accompanying drawings wherein:

FIG. 1 is a perspective view of one embodiment of the subject invention, showing the freeze drying chamber open and the tissue platen removed from the chamber and resting on the top surface of the apparatus.

FIG. 2 is an exploded view in perspective and partially cut away to show the interior of the freeze drying chamber of the tissue dryer of FIG. 1;

FIG. 3 is a side elevational view in cross section of the tissue dryer shown in FIG. 1.

Referring now to FIG. 1, there is shown a tissue dryer assembly 10, having a freeze drying chamber 37 opening onto an upper surface 19. The environment within the freeze drying chamber 37 is maintained through a control panel 23 located at the front of the tissue drying assembly 10 and controls the various parameters, such as temperature, pressure and the like, within the chamber 37. The freeze drying chamber 37 communicates with a source of vacuum (not shown) through opening 35 and an appropriate connection such as tubing 41. Within the chamber 37, a tissue platen or specimen plate 25 may hold perforated specimen cups in a manner to be described. This tissue platen 25 may be easily placed in the chamber and removed from the chamber through a handle 36 which is removably secured to the tissue platen through a suitable mating arrangement such as tapped hole 38. The chamber is made vacuum-tight through a transparent top in a manner to be described. Paraformaldehyde vapors may be introduced into the chamber 37 for formaldehyde-induced-fluorescense from a suitably heated supply of paraformaldehyde retained in test tube 40 and supplied to the freeze drying chamber while under vacuum in a manner known in the art.

The freeze drying chamber 37 is shown in more detail in FIGS. 2 and 3 wherein the chamber is shown to be formed of exterior walls 20 immediately surrounding the chamber 37. Refrigerant coils 22 are immediately adjacent and intimately contact the interior of the chamber 37 for better thermal transfer to the chamber 37. Insulation 21 fills the chamber walls 20, thereby embedding the refrigerant coils and directing any cold generated by the refrigerant coils to the interior of the chamber 37 and effectively insulating the cold temperatures of the freeze drying chamber 37 from ambient conditions.

The assembly top surface 19 is secured to the upper portion of the chamber walls 20. Mounted about the upper chamber opening is a rim gasket 17 of resilient material, preferably silicone, which will resist the extremes in temperature and the corrosive effects of the vapors subliming under vacuum. A seat 18 is provided on the rim gasket 17 for the support of the top plate 14, which is preferably formed of clear polycarbonate or polymethylpentene for allowing a complete view of the operations within the freeze drying chamber 37. A finger groove 16 is provided on the periphery of the cover plate 14 to allow easy manipulation of the cover plate 14 when opening the chamber. A tissue platen support plate 27 of generally circular and plate-like dimensions is rigidly secured at the bottom of the chamber 37 though spaced from the bottom in a manner which will be explained.

The support plate 27 is preferably of copper, although other durable thermally-conductive materials may be used. The upper surface 28 of the support plate 27 is machined to a close tolerance thereby forming a substantially flat upper surface. The support plate 27 is supported by tubes or ducts 30 and 33 which extend on a horizontal plane through the freeze drying chamber 27 (FIG. 3). The underside of the support plate 27 is mechanically affixed to each of the ducts 30 and 33 through brazing, welding or the like, which operations are reliably conducted with copper and assure excellent thermal contact.

A heating means 31 may be placed within the cylinder 30 and underneath the support plate 27. This heating means 31 may take the form of an electrical resistance heating cartridge which can be controlled by a variable resistor element from the front panel 23 as is well known in the art. The heat supplied to the support plate 27 can thus be controlled by the rotation of a dial on the front panel 23. Any other means of supplying a controlled source of heat to the support plate may be used. When the use of a heating cartridge is preferred, opposing ends of the cylinder 30 will be open or capable of being opened by the removal of a cap or the like, thereby allowing the heating cartridge to be inserted in one end. Should the cartridge become stuck or otherwise rendered immovable in the cylinder 30, it may be easily pushed out with an appropriate utensil from the other open end.

A temperature probe 33 may be placed in duct 31 for sensing the temperature of the support plate. The temperature probe 33 is connected to an appropriate readout device on the control panel 23 for use in conjunction with the heating means 31 to control the support plate temperature. The duct 31 also may be open at opposing ends to allow the easy removal of the temperature probe 33 as with the heating cartridge 31.

The tissue platen or specimen plate 25 is placed on the support plate 27 for maximum surface contact and transfer of heat in a manner to be explained. The excellent thermal contact of all components for specimen support assures a marked increase in effectiveness when controlling the temperature of the contents of the specimen plate.

The specimen plate 25 may be easily placed in the chamber and removed by hand, however, should the platen 25 be too cold or too hot for manual removal, a threaded lifting handle is provided, which attaches to the top of the peripheral walls of the specimen plate 25.

The specimen plate 25 is formed of Aluminum. The underside of the specimen plate 25 is recessed approximately the thickness of the support plate 27, thereby forming a recessed area 29 roughly the size of the support plate. The upper surface of the specimen plate is also recessed to provide a plate surface 26 for the reception of the tissue specimens in specimen cups. The plate surface is recessed a sufficient amount behind peripheral walls 27 which are thick enough so that substantially all lateral thermal gradients on the plate surface 26 and external temperature effects on the specimens within the specimen cups are eliminated.

For maximum efficiency of thermal transfer between the support plate and the specimen plate, the upper surface of the support plate 27 is carefully wiped free of any foreign material which might interfere with the quality of the fit between itself and the specimen plate 25 it supports. Before placing the specimen plate 25 in position, apply a thin film of high vacuum grease to its underside to even out any irregularities in the plate surface 29 and further improve surface contact. The specimen plate 25 is placed gently on the support plate 27 with a slight turning motion until it is felt to settle into firm contact with plate 27. Once the specimen plate 25 is in full contact with the support plate 27 and the specimen cups and paraffin are placed on the plate surface 26, the horizontal lip 18 of the rim gasket 17 is lightly greased with high-vacuum grease, and the clear plastic chamber cover 14 is placed into position, to seal the chamber.

With the cover 14 in place, the refrigeration unit may be turned on. The specimen plate 25 and all vapor condensing surfaces 34 should reach the appropriate low temperature within fifteen to twenty minutes as sensed by the temperature probe 33 and indicated in the control panel 23. After the specimens are in a frozen state the vacuum pump may be activated. The desired vacuum level should be reached in five to ten minutes, also indicated on the control panel 23 by an appropriate gauge. Under such a vacuum, the moisture content will sublime and condense on the interior walls 34 of the chamber 37. When the specimens have been under such vacuum conditions for a length of time sufficient to be fully dried, the heat cartridge 32 is turned on and adjusted to the desired temperature (generally 80° C.) in the manner set forth above. The time under vacuum will vary depending on the mass of specimen to be dried and the temperature of the chamber. The rising temperature of the support plate 27 is efficiently transferred to the specimen plate, melting the paraffin in the specimen plate. Control of the paraffin temperature is important, as it easily foams, and therefore the efficient heat transfer found in the specimen holding assembly aids in coordinating sensing the temperature of the paraffin and manually increasing or decreasing the heat input.

The paraffin, when melted, permeates the perforated specimen cups and impregnates or engulfs the tissue specimens in the commonly known manner.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A freeze dryer assembly for drying and impregnating tissue specimens with paraffin or resin, said assembly including a vacuum chamber having an outlet for connection to a source of vacuum, a closure means for fluid-tightly sealing said chamber, chamber walls, cooling means integral with said chamber walls for cooling said chamber to a desired temperature under vacuum, a heating means, a support plate fixedly mounted on said heating means for the support of a specimen holder, said specimen holder being mateable with said support plate for substantial surface contact of said specimen holder with said support plate, said specimen holder and support plate formed of materials of good thermal conductivity, said specimen holder having peripheral walls about an upper surface, said peripheral walls being of a height and a thickness effective to minimize the effect of thermal differentials within said chamber on said upper surface of said specimen holder and thereby being capable of retaining said upper surface of said specimen holder at a substantially constant temperature.

2. The freeze dryer assembly of claim 1 wherein said heating means comprises a duct through said chamber, said duct opening onto each of opposite sides of the exterior of said chamber, and a removable heating element disposed between said openings within said duct.

3. The freeze dryer assembly of claim 1 wherein an upper surface of said support plate is machined to provide a substantially flat upper surface.

4. A tissue specimen platen assembly for use in an enclosed chamber of a freeze drying assembly, said chamber having an outlet for connection to a source of vacuum and having a support plate fixedly mounted within said freeze drying assembly and a platen for holding specimens, said platen mounted on said support plate in a mating relationship for high thermal conductivity between said platen and support plate, for the easy removal of said platen from said support plate, said platen having a recess on an underside, said recess accepting said support plate for maximum engagement of opposing surfaces and maximum transfer of heat, heating means fixedly mounted to said support plate for supplying heat thereto, refrigeration means attached to said freeze drying assembly for cooling purposes, said platen having peripheral walls of sufficient thickness and height to substantially preclude temperature influences external to said platen from affecting the contents of said platen within said peripheral walls.

5. The freeze drying assembly of claim 4 wherein said platen is formed of Aluminum for high thermal conductivity.

6. The freeze drying assembly of claim 4 wherein said support plate is formed of copper for high conductivity and ease of permanent reliable mechanical connection thereto.

7. The freeze drying assembly of claim 4 wherein a handle is removably attachable to said platen for ease in removal of said platen from said freeze drying assembly.

8. A freeze dryer assembly having a vacuum chamber bounded by chamber walls, a cover assembly for fluid-tightly sealing said vacuum chamber, a refrigerating means for cooling said vacuum chamber to a desired temperature, a means for applying vacuum to said vacuum chamber and a platen within said vacuum chamber for receiving specimens, wherein the improvement lies in a heating means for controllably heating said platen, said heating means comprising a duct passing into said vacuum chamber through each of opposite sides of said chamber walls, said duct communicating with said platen through a thermally conductive path for the efficient transfer of heat from said duct to said platen, said duct accepting a source of heat powered and controlled externally of said vacuum chamber.

9. A freeze dryer assembly for drying and impregnating tissue specimens with paraffin or resin, said assembly including a vacuum chamber having an outlet for connection to a source of vacuum, a closure means for fluid-tightly sealing said chamber, cooling means for cooling said chamber to a desired temperature under vacuum, a heating means, a support plate fixedly mounted on said heating means for the support of a specimen holder, said specimen holder being matable with said support plate for substantial surface contact of said specimen holder with said support plate, said specimen holder and support plate formed of materials of good thermal conductivity, a temperature sensing means comprising a duct fixed mounted to an underside of said support plate and opening onto opposite sides of the exterior of said chamber, and a temperature measuring device removably mounted within said duct, said specimen holder having peripheral walls about an upper surface, said peripheral walls being of a height and a thickness effective to minimize the effect of thermal differentials within said chamber on said upper surface of said specimen holder and thereby being capable of retaining said upper surface of said specimen holder at a substantially constant temperature.

* * * * *